United States Patent
Beckmann et al.

(10) Patent No.: US 6,730,132 B1
(45) Date of Patent: May 4, 2004

(54) REDUCTION CLEARING OF POLYESTER TEXTILES

(75) Inventors: Eberhard Beckmann, Neustadt (DE); Rudolf Krüger, Weisenheim (DE); Ulrich Karl, Ludwigshafen (DE); Claus Tritschler, Heddesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/048,029

(22) Filed: Jan. 22, 1999

(30) Foreign Application Priority Data

Jul. 23, 1996 (DE) .......................... 196 29 453

(51) Int. Cl.⁷ .............. D06P 3/52; D06P 5/04; D06L 1/12
(52) U.S. Cl. ............ 8/137; 8/110; 8/588; 8/592; 8/602; 8/142; 8/922
(58) Field of Search ............... 8/922, 137, 110, 8/588, 592, 602, 142

(56) References Cited

U.S. PATENT DOCUMENTS 4,227,881 A  * 10/1980 Fono
4,400,174 A    8/1983 Blum et al.

FOREIGN PATENT DOCUMENTS

| DE | 27 44 607  | 3/1979  |
| FR | 2 379 645  | 9/1978  |
| GB | 1 139 558  | 1/1969  |
| JP | 02 091285  | 3/1990  |
| JP | 05 272075  | 10/1993 |

OTHER PUBLICATIONS

T.M. Baldwinson: "Some observations on colour fastness to washing with particular references to disperse dyes on polyester" Journal of the Society of Dyers and Colourists-vol. 91, No. 4, pp. 97–102 04/75. , Dr. S. Heimann: "Neue moeglichkeit zur nachbehandlung gefaerbter polyesterfasern" Chemiefasern Textil–Industrie, vol. 30, No. 11, pp. 898–901 11/80 no translation.

* cited by examiner

*Primary Examiner*—Margaret Einsmann
(74) *Attorney, Agent, or Firm*—Oblon, Spivak, McClelland, Maier & Neustadt, P.C.

(57) ABSTRACT

A process for reduction clearing dyed or printed polyester textiles, which comprises adding, to an acidic dyeing liquor or a wash bath, an aftertreatment composition comprising as components a) at least one compound of the formula (I)

$$A_m[(CR^1R^2)_mSO_2M]_{p,q} \quad (I)$$

where A is $NR^3_{3-q}$ or $OR^4_{2-p}$; p,q means q when A is $NR^3_{3-q}$, and p when A is $OR^4_{2-p}$; $R^1$, $R^2$, $R^4$ are each hydrogen or $C_1$–$C_6$-alkyl; $R^3$ represents identical or different radicals selected from the group consisting of hydrogen, $C_1$–$C_{20}$-alkyl, $C_3$–$C_8$-cycloalkyl opt. substituted by from one to three $C_1$–$C_4$-alkyl radicals; M is the equivalent of an ammonium, alkali metal or a kaline earth metal ion; m is 0 or 1; p is 1 or 2; and q is 1, 2 or 3, subject to the provisos that at least one of $R^1$, $R^2$, $R^4$ is $C_1$–$C_6$-alkyl when A is $OR^4_{2-p}$ and that, if m is 0: the compound of formula (I) is $S_2O_4M_2$, and the compound of the formula (I) is used together with sufficient acid acceptor to raise the pH of the dyeing liquor or of the wash bath by from 1 to 3 units, b) optionally at least one compound of the formula (II)

$$A[CR^1R^2)SO_3M]_{p,q} \quad (II)$$

where A, $R^1$, $R^2$, $R^3$, $R^4$, M, p,q p and q are each as defined for the formula (I), although the specific choice of these variables does not have to be the same for the compounds of the formulae (I) and (II)

c) and optionally further additives.

16 Claims, No Drawings

REDUCTION CLEARING OF POLYESTER TEXTILES

The present invention describes a process for reduction clearing dye or printed polyester textiles. It further relates to mixtures useful as aftertreatment compositions in the process of the invention, its preferred components and its preferred use form and quantity.

In vat dyeing, cellulosic textiles are customarily dyed by converting suitable dyes by reduction in a strongly alkaline medium into their soluble leuco form, which, after penetrating the fiber, is converted back into the insoluble dye by atmospheric oxidation. The reductant used is usually sodium dithionite, but the use of sulfinates is known too, from GB-3-829 177, for related printing applications. Mixtures of dithionite with sulfinates or sulfonates are described in U.S. Pat. No. 3,265,459, U.S. Pat. No. 3,645,665 and U.S. Pat. No. 3,798,172 as useful reductants for cellulose dyeing.

By contrast, polyester textiles are exclusively dyed in an acidic medium. The method employed is the high temperature exhaust process, the thermosol process or the superheated steam fixation process. In the first process, the textile is dyed in a dyebath in a pressure vessel at a pH of about 3–6 and a temperature of about 120–140° C. This treatment causes the disperse dye to diffuse into the plasticized polyester fiber to form a molecular dispersion in the polymer matrix. The completion of the dyeing step is usually followed by a preclear with fresh water and finally by an alkaline reduction clear in a wash bath, for which purpose it is customary to use sodium dithionite and caustic soda in aqueous solution.

In the thermosol and superheated steam fixation processes, too, the preclear is followed by alkaline reduction clearing.

As in the high temperature exhaust process, in the thermosol and superheated steam fixation processes the aftertreatment used is predominantly an aqueous solution of caustic soda and sodium dithionite. The pH of the reduction clearing bath is therefore high, about 12–13. Wash baths which contain sodium hydroxymethanesulfinate (Rongalit®c, Superlite®c) optionally in mixtures with sodium hydroxymethanesulfonate or dithionite-formaldehyde condensates, and which in specific cases can also be rendered acidic by addition of strong organic or inorganic acids are described in JP-A-05 272 075-A, JP-A-02 300 391, JP-A-04 146 279, JP-A-01 028 090, JP-A-02 091 285, JP-A-57 006 188, JP-A-57 066 189, JP-A-60 162 889. However, these washing systems do not meet the high requirements demanded of aftertreatment compositions in respect of the achievement of high color fastnesses on polyester textiles.

Disadvantages of the traditional high temperature exhaust process are
- high time, water and energy intensity through the pH change from acid to alkaline
- high salt loadings in the dyehouse wastewater and dye residues which color the wastewater
- high autoignition tendency of hydrosulfite in bulk, and
- a relatively rapid exhaustion of the reductive wash bath through atmospheric oxidation.

The thermosol and the superheated steam fixation processes likewise have the disadvantage of insufficient air stability of the wash baths, so that accurate dosing of the reductant cannot be accomplished under plant conditions without analysis. As a consequence, it is not always possible to avoid incompletely destroyed dye residues staining the white ground.

It is an object of the present invention to provide a simplified process for dyeing polyester textiles—without a costly interim rinse and a separate clear—to save time, water and energy. Furthermore, colorless, low-salt wastewaters shall result, and the aftertreatment compositions to be used in the dyeing liquor or in the wash bath shall be simple to handle, high yielding, simple to meter and possessed of an effective clearing action.

We have found that this object is achieved by a process for reduction clearing dyed or printed polyester textiles, which comprises adding, to the acidic dyeing liquor or the wash bath, an aftertreatment composition comprising as components a) at least one compound of the formula (I)

$$A_m[(CR^1R^2)_mSO_2M]_{p,q} \quad (I)$$

where
A is $NR^3_{3-q}$ or $OR^4_{2-p}$
$R^1$, $R^2$, $R^4$ are each Hydrogen or $C_1-C_6$-alkyl
$R^3$ represents identical or different radicals selected from the group consisting of hydrogen, $C_1-C_{20}$-alkyl, $C_3-C_8$-cycloalkyl opt. substituted by from one to three $C_1-C_4$-alkyl radicals
M is the equivalent of an ammonium, alkali metal or alkaline earth metal ion
m is 0 or 1
p is 1 or 2
q is 1, 2 or 3
subject to the provisos that at least one of $R^1$, $R^2$, $R^4$ is $C_1-C_6$-alkyl when A is $OR^4_{2-p}$ and that, if m is 0:
p, q are each 2 and
the compound of he formula (I) is used together with sufficient acid acceptor to raise the pH of the dyeing liquor or of the wash bath by from 1 to 3 units, b) optionally at least one compound of the formula (II)

$$A[(CR^1R^2)SO_3M]_{p,q} \quad (II)$$

where A, $R^1$, $R^2$, $R^3$, $R^4$, M, p and q are each as defined for the formula (I), although the specific choice of these variables does not have to be the same for the compounds of the formulae (I) and (II)

c) and optionally further additives.

When the process of the invention is to be carried out with mixtures comprising ammonium, alkali metal or alkaline earth metal dithionites—where m in the formula (I) is 0, that is—the acid acceptors used are preferably ammonium, alkali metal or alkaline earth metal bicarbonate, carbonate, oxide, hydroxide, bisulfite, sulfite, hydrogenphosphate or phosphate, the use of the alkali metal and alkaline earth metal bicarbonates and carbonates being particularly preferred. Normally the sodium dithionite commercially available as "hydrosulfite" will be used. This sodium dithionite generally has a technical grade purity of more than 80%. Its use in the reduction clearing process described herein is preferred for cost reasons. However, special requirements may justify the use of other alkali metal and also alkaline earth metal or ammonium dithionites or mixtures thereof.

Suitable ammonium dithionites are not only $NH_4^{\oplus}$ but also, for example, $NL_4^{\oplus}$ compounds, wherein the substituents L represent identical or different radicals selected from the group consisting of hydrogen and $C_1-C_6$-alkyl in which nonadjacent CH and $CH_2$ groups may be replaced by N on the one hand or NH or O on the other and $CH_3$ groups by $NH_2$ or OH. Examples thereof are the mono-, di-, tri- and tetraethanolammonium compounds, but also the corresponding salts of ethylenediamine, diethylenetriamine and triethylenetetramine. It is also possible to use the salts of the condensation products of ammonia with diethylene glycol such as $H_2N(C_2H_4)O(C_2H_4)OH$, $HN[(C_2H_4)O(C_2H_4)(OH]_2$ or $N[(C_2H_4)O(C_2H_4)OH]_3$.

Suitable acid acceptors in addition to the aforementioned substances also include their mixtures. The only important criterion is to ensure a buffering of the acidic dyeing liquor by about 1–3 pH units in order that the reduction of excess dye by the dithionite may be ensured.

Normally, the desired pH change is ensured by the use of dithionites and acid acceptor in a weight ratio within the range from 3:1 to 1:1, which is why this mixing ratio is indeed preferred.

Depending on the specific requirements, it can also be sensible to add salts of complexing agents such as, for example, nitrilo-triacetic acid (NTA, $N(CH_2COOH)_3$), ethylenediaminetetraacetic acid (EDTA, $[CH_2N(CH_2COOH)_2]_2$), diethylenetriaminepentaacetic acid (DTPA, $HOOCCH_2N[(CH_2)_2N(CH_2COOH)_2]_2$), hydroxyethylethylenediamine triacetic acid (HEDTA, $HO(CH_2)_2N(CH_2COOH)(CH_2)_2N(CH_2COOH)_2$), propylenediaminetetraacetic acid (PDTA, $(HOOCCH_2)_2N(CH_2)_3N(CH_2COOH)_2$) or β-alaninediacetic acid $((HOOCCH_2)_2N(CH_2)_2COOH)$ as a buffer. These are marketed under the brandname of Trilon®, for example. It is also possible to use mixtures between these complexing agents alone or with other acid acceptors.

If, in addition, surfactants or dispersants are used in the aftertreatment, it is possible, if necessary, to sequester any interfering heavy metal ions or else reduce the water hardness by the use of such complexing agents.

Preferred amines have $C_1$–$C_{20}$-alkyl radicals and also $C_3$–$C_8$-cycloalkyl radicals, which can opt. additionally be substituted by from one to three further $C_1$–$C_4$-alkyl radicals.

If primary amines are used, the reaction with $HOCH_2SO_3M$ yields the N-alkylated aminomethanesulfonates $R^3NHCH_2SO_3M$, for example. The radicals $R^3$ include not only linear $C_1$–$C_{20}$-alkyl chains such as methyl, ethyl, propyl, butyl, pentyl, hexyl, etc. up to eicosyl, but also branched $C_1$–$C_{20}$ radical such as, for example, the various methylbutyls, ethylbutyls, methylpentyls, ethylpentyls, methylhexyls, ethylhexyls, methylheptyls, ethylheptyls etc. This gives rise to sulfonates such as $(H_3C)NHCH_2SO_3M$, $(H_5C_2)NHCH_2SO_3M$, $(H_7C_3)NHCH_2SO_3M$, $(H_9C_4)NHCH_2SO_3M$, $(H_{11}C_5)NHCH_2SO_3M$, $(H_{13}C_6)NHCH_2SO_3M$ to $(H_{41}C_{20})NHCH_2SO_3M$ but also 1-, 2-, 3-methylbutylaminomethane sulfonate, 1-, 2-, 3-ethylbutylaminomethanesulfonate, 1-, 2-, 3-, 4-methylpentylaminomethanesulfonate, 1-, 2-, 3-, 4-ethylpentylaminomethanesulfonate, 1-, 2-, 3-, 4-, 5-methylhexylaminomethanesulfonate, 1-, 2-, 3-, 4-, 5-ethylhexylaminomethanesulfonate, 1-, 2-, 3-, 4-, 5-, 6-methylheptylaminomethanesulfonate, 1-, 2-, 3-, 4-, 5-, 6-ethylheptylaminomethanesulfonate etc. In the case of the opt. $C_1$–$C_4$-alkyl-substituted $C_3$–$C_8$-cycloalkyl radicals, the reaction yields, exemplified for the cyclohexyl, the following sulfonates:

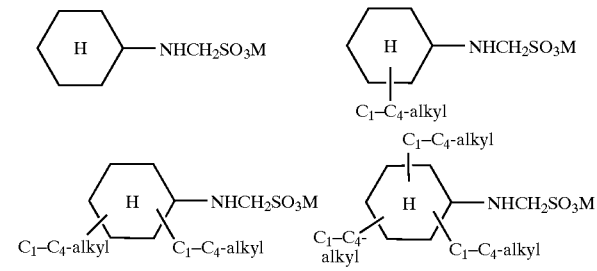

Furthermore, the aftertreatment-composition based on dithionites and acid acceptors may also include sulfonates conforming to the formula (II). Compounds such as, for example, $HOCH(CH_3)SO_3M$ to $HOCH(C_6H_{13})SO_3M$ can be prepared, for example, by addition of bisulfite $MHSO_3$, where M is preferably an alkali metal such as sodium, to acetaldehyde or enanthaldehyde, $C_6H_{13}CHO$. These sulfonates are also formed in the reaction of aldehydes with dithionites, in mixture with the corresponding sulfinates and depending on the reaction managememt and the molar ratios.

Reaction of hydroxyalkanesulfonates with ammonia in varying mixing ratios gives the amino-, imino- and nitrilosulfonates. Starting from the corresponding hydroxyalkanesulfonates, these are for example compounds $HN(CH_2SO_3M)_2$, $N(CH_2SO_3M)_3$, $H_2NCH(CH_3)SO_3M$, $HN(CH(CH_3)SO_3M)_2$, $N(CH(CH_3)SO_3M)_3$ to $H_2NCH(C_6H_{13})SO_3M$, $HN(CH(C_6H_{13})SO_3M)_2$, and $N(CH(C_6H_{13})SO_3M)_3$, partly also in mixture with the corresponding starting sulfonates. It is further possible to use $H_2NCH_2SO_2M$.

The corresponding N-substituted amino- or aminoalkanesulfonates can be obtained by reacting hydroxyalkanesulfonates with primary or secondary amines, for example.

Corresponding iminoalkanesulfonates can be prepared by replacing the amino hydrogen by a further alkanesulfonate group, for example. The amount of alkylamine and hydroxyalkanesulfonate for the synthesis must therefore also be selected accordingly, and the hydroxyalkanesulfonate reactant can also be a mixture of various hydroxyalkanesulfononates. In the case of amines symmetrically substituted by alkanesulfonate radicals, the reaction thus yields aminoalkanesulfonates such as $(H_3C)N(CH_2SO_3M)_2$, if the starting materials used are methylamine and hydroxymethanesulfonate in a molar ratio of 1:2. All the above-recited aminomethanesulfonates can also be converted into the corresponding iminomethanesulfonates in a similar manner. If secondary amines are used, the diversity of the compounds is determined not just, as previously indicated, by the possibility of using mixtures of various hydroxyalkanesulfonates, but additionally also by the possibility of the choice of different alkyl radicals $R^3$ on the starting amine. However, because of the multiplicity of the various N,N-disubstituzed aminoalkane-sulfonates obtainable by reaction of $R^3_2NH$ with hydroxyalkane-sulfonates (or mixtures thereof), no further details will be given here.

It may further be noted that the reaction of ammonia or primary amines $R^3NH_2$ with various hydroxyalkanesulfonates also makes it possible to prepare "molecularly mixed" nitriloalkane- or iminoalkane-sulfonates in a specific manner.

For two hydroxyalkanesulfonates—hereinafter abbreviated to $HOAlkSO_3(1)$ and $HOAlkSO_3(2)$—the number and type of the desired compounds may be illustrated by the schemes (a) and (b):

(a) $NH_3+HOAlkSO_3(1) \rightarrow H_2NAlkSO_3(1)+H_2O$
$H_2NAlkSO_3(1)+2HOAlkSO_3(2) \rightarrow N(AlkSO_3(1))(AlkSO_3(2))_2+2H_2O$ or $NH_3+HOAlkSO_3(2) \rightarrow H_2NAlkSO_3(2)+H_2O$ $H_2NAlkSO_3(2)+2HOAlkSO_3(1) \rightarrow N(AlkSO_3(2))(AlkSO_3(1))_2+2H_2O$ (b) $R^3NH_2+HOAlkSO_3(1)+HOAlkSO_3(2) \rightarrow R^3N(AlkSO_3(1))(AlkSO_3(2))+2H_2O$ Of course, such "intramolecularly mixed" sulfonates shall also be embraced by the invention.

Preference is given to using the sodium sulfonates and particularly preferably the compounds $H_2NCH_2SO_3Na$, $HN(CH_2SO_3Na)_2$, $N(CH_2SO_3Na)_3$, $HOCH(CH_3)SO_3Na$, $H_2NCH(CH_3)SO_3Na$, $HN(CH(CH_3)SO_3Na)_2$, $N(CH(CH_3)SO_3Na)$ and sodium salts of 1-, 2-, 3-, 4- and 5-ethylhexylamino-methanesulfonic acid and -ethanesulfonic acid.

The preferred molar ratio of dithionite to sulfonaze is within the range from 20:1 to 1:20, especially within the range from 10:1 to 1:10.

The hydroxy-, amino-, imino- and nitrilo-alkanesulfinates to be used according to the invention, for which m is 1 in the formula (I), are formally derivable from the above-recited sulfonates by replacing the $SO_3M$ group with an $SO_2M$ group. This produces, for example, compounds such as $HOCH(CH_3)SO_2M$ to $HOCH(C_6H_{13})SO_2M$ but also $H_2NCH_2SO_2M$, $HN(CH_2SO_2M)_2$, $N(CH_2SO_2M)_3$, $H_2NCH(CH_3)SO_2M$, $HN(CH(CH_3)SO_2M)_2$, $N(CH(CH_3)SO_2M)_3$ to $H_2NCH(C_6H_{13})SO_2M$, $HN(CH(C_6H_13)SO_2M)_2$, $N(CH(C_6H_{13})SO_2M)_3$. By replacing the amino hydrogen with one or, where possible, two radicals $R^3$ it is possible to prepare the N-substituted sulfinates. As in the case of the abovementioned sulfonates, $R^3$ preferably represents linear or branched $C_1$–$C_{20}$-alkyl radicals and also unsubstituted or $C_1$–$C_4$-alkyl-monosubstituted, -disubstituted or -trisubstituted $C_3$–$C_8$-cycloaliphatic radicals.

Exemplified for the aminomethanesulfinate, $H_2NCH_2SO_2M$, this gives rise to the N-substituted compounds such as methyl-, ethyl- up to eicosyl-aminomethanesulfinate but also 1-, 2-, 3-methylbutyl-, 1-, 2-, 3-ethylbutyl-, 1-, 2-, 3-, 4-methylpentyl-, 1-, 2-, 3-, 4-ethylpentyl-, 1-, 2-, 3-, 4-, 5-methylhexyl-, 1-, 2-, 3-, 4-, 5-ethylhexyl-aminomethanesulfinate, etc. The cyclohexylamino-methanesulfinates with or without substitution on the cyclohexane ring, for example, can be derived similarly to the method recited in connection with the sulfonates.

Similarly to the iminoalkanesulfonates mentioned, twofold replacement of hydrogens in the primary amine $R^3NH_2$ by alkanesulfinate radicals will of course also yield corresponding iminoalkanesulfinates, and if the synthesis is carried out from the amine $R^3NH_2$ and a hydroxyalkanesulfinate or a mixture of sulfinates it is also possible to prepare an imino/aminoalkanesulfinate mixture, depending on the mixing ratio. The use of this mixture in the process of the invention is likewise possible. As regards the N,N-disubstituted aminoalkanesulfinates, they are subject, mutatis mutandis, to the comments made above in relation to the sulfonates.

If aftertreatment compositions based on sulfinates are used together with at least one sulfonate of the formula (II), a molar ratio of sulfinate to sulfonate within the range from 20:1 to 1:20, is preferred and a molar ratio within the range from 10:1 to 1:10 is particularly preferred. In addition, acid acceptors can be included here too.

Mixtures of alkanesulfinates with alkanesulfonates, for example in a molar ratio of 1:1, are easily obtainable by reacting the aldehydes $R^1$—CHO or ketones $R^1$—CO—$R^2$ with dithionites in a carbonyl compound/dithionite ratio of 2:1. For instance, reaction of sodium dithionite with acetaldehyde, propionaldehyde, butyraldehyde, n-valeraldehyde, capronaldehyde or enanthaldehyde yields mixtures of sulfinates and sulfonates, which conform to the formulae $HOCH(CH_3)SO_2M$ or $HOCH(CH_3)SO_3M$, $HOCH(C_2H_5)SO_2M$ or $HOCH(C_2H_5)SO_3M$, $HOCH(C_3H_7)SO_2M$ or $HOCH(C_3H_7)SO_3M$, $HOCH(C_4H_9)SO_2M$ or $HOCH(C_4H_9)SO_3M$, $HOCH(C_5H_{11})SO_2M$ or $HOCH(C_5H_{11})SO_3M$ and $HOCH(C_6H_{13})SO_2M$ or $HOCH(C_6H_{13})SO_3M$, where M is one equivalent of an ammonium, alkali metal or alkaline earth metal ion or—if sodium dithionite is used—sodium, of course. The use of aldehydes having branched chains is also possible, so that the resulting sulfinates and sulfonates have $C_6$ radicals $R^1$ such as 1-, 2-, 3-, 4-methylpentyl and 1-, 2-ethylbutyl, $C_5$ radicals such as 1-, 2-, 3-methylbutyl (isoamyl) and 1-ethylpropyl, and $C_4$ radicals 1-, 2-methylpropyl (isobutyl).

Switching from aldehydes to ketones as reaction partners for dithionite, the choice is of symmetrical compounds starting with methyl methyl ketone, ie. acetone, through to hexyl hexyl ketone, $(H_{13}C_6)CO(C_6H_{13})$, and the larger group of the asymmetrical ketones starting with methyl ethyl ketone through to methyl hexyl ketone via ethyl propyl ketone to ethyl hexyl ketone etc. through to, finally, pentyl hexyl ketone. This gives rise to the corresponding sulfinates/sulfonates $HOC(CH_3)_2SO_2M/HOC(CH_3)_2SO_3M$ to $HOC(C_6H_{13})_2SO_2M/HOC(C_6H_{13})_2SO_3M$ and also the asymmetrically substituted compounds $HOC(CH_3)(C_2H_5)SO_2M/HOC(CH_3)(C_2H_5)SO_3M$ to $HOC(CH_3)(C_6H_{13})SO_2M/HOC(CH_3)(C_6H_{13})SO_3M$, $HOC(C_2H_5)(C_3H_7)SO_2M/HOC(C_2H_5)(C_3H_7)SO_3M$ to $HOC(C_2H_5)(C_6H_{13})SO_2M/HOC(C_2H_5)(C_6H_{13})SO_3M$ etc. up to $HOC(C_5H_{11})(C_6H_{13})SO_2M/HOC(C_5H_{11})(C_6H_{13})SO_3M$. Here too it is of course possible, as with the abovementioned reactions of aldehydes, for the correspondingly branched aliphatic radicals to appear.

Reacting the unsubstituted or substituted hydroxymethanesulfinates and hydroxymethanesulfonates with ammonia will produce, depending on the ratio of the reactants, mono-, di- or trisubstituted amines of the general formulae $H_2NCR^1R^2SO_2M$ or $H_2NCR^1R^2SO_3M$, $HN(CR^1R^2SO_2M)_2$ or $HN(CR^1R^2SO_3M)_2$ and $N(CR^1R^2SO_2M)_3$ or $N(CR^1R^2SO_3M)_3$. A mixture of hydroxymethanesulfinate, $HOCH_2SO_2M$, with hydroxymethanesulfonate, $HOCH_2SO_3M$, leads in the reaction with ammonia and depending on the sulfinate/sulfonate:ammonia ratio to the corresponding aminomethanesulfinate/sulfonate, iminomethanesulfinate/sulfonate, nitrilomethansulfinate/sulfonate mixtures $H_2NCH_2SO_2M/H_2NCH_2SO_3M$, $HN(CH_2SO_2M)_2/HN(CH_2SO_3M)_2$, or $N(CH_2SO_2M)_3/N(CH_2SO_3M)_3$. Use of symmetrically or asymmetrically substituted hydroxyalkylsulfinates/sulfonates as exemplified above produce, for example for the starting compounds $HOC(CH_3)_2SO_2M/HOC(CH_3)_2SO_3M$, the following compounds $H_2NC(CH_3)_2SO_2M/H_2NC(CH_3)_2SO_3M$, $HN(C(CH_3)_2SO_2M)_2/HN(C(CH_3)_2SO_3M_2$, $N(C(CH_3)_2SO_2M)_3/N(C(CH_3)_2SO_3M)_3$ or, for example for the starting compounds $HOC(CH_3)(C_2H_5)SO_2M/HOC(CH_3)(C_2H_5)SO_3M$, the compounds $H_2NC(CH_3)(C_2H_5)SO_2M/H_2NC(CH_3)(C_2H_5)SO_3M$, $HN(C(CH_3)(C_2H_5)SO_2M)_2/HN(C(CH_3)(C_2H_5)SO_3M)_2$ and $N(C(CH_3)(C_2H_5)SO_2M)_3/N(C(CH_3)(C_2H_5)SO_3M)_2$.

If desired, it is possible to use other mixtures of sulfinates optionally together with mixtures of sulfonates. Mixtures of sulfinates with sulfonates are also simple to prepare by means of incomplete reactions. The use of a mixture of $HOCH(CH_3)SO_2M/HOCH(CH_3)SO_3M$ and use of a quantity of ammonia which is not sufficient to obtain corresponding nitrilo compounds will, after the reaction has ended, lead not only to the reaction product $N(CH(CH_3)SO_2M)_3/N(CH(CH_3)SO_3M)_3$ but also to the incompletely converted starting components $HOCH(CH_3)SO_2M$ and $HOCH(CH_3)SO_3M$. In the same way, mutatis mutandis, it is also possible to set any ratio of, for example, amino or imino to nitrilosulfinates/sulfonates. More complex mixtures are obtainable by using mixed hydroxyalkylsulfinate/sulfonate starting components. For instance, the sulfinates $HO(CH_3)_2SO_2M$ and $HOCH(CH_3)SO_2M$ can be obtained in mixture with the sulfonates $HO(CH_3)_2SO_3M$ and $HOCH(CH_3)SO_3M$ by reaction of an acetone/acetaldehyde mixture with dithionite and, in accordance with the above, be reacted with a deficiency of ammonia to form the nitrilo products mixed with the starting components.

If the hydroxyalkanesulfinates, if desired mixed with the sulfonates, are reacted, not with ammonia, but with a primary or secondary amine $R^3NH_2$ or $R_2^3NH$, the corresponding N-alkylated products are obtained opt. in mixture with their underlying hydroxyalkanesulfinates/sulfonates. However, in the case of the primary amines $R^3NH_2$, only N-alkylated iminoalkane- and in the case of the secondary amines $R_2^3NH$ only N-alkylated aminoalkanesulfinates/sulfonates are obtainable.

For dithionite-based aftertreatment compositions, various N-alkylated derivatives, differing in the radicals $R^3$, were exemplified above in relation to the $HOCH_2SO_3M$ parent species. Of course, all the hydroxysulfinates/sulfonates already mentioned, which are obtainable by reaction of aldehydes/ketones or their mixtures with dithionites, can be reacted with these amines to form the N-substituted amino- or imino-sulfinates/sulfonates. Therefore, of the multiplicity of possible sulfinates/sulfonates to be used according to the invention, only one hydroxyethanesulfinate/sulfonate mixture of the various reaction products from the reaction with, for example, 2-ethylhexilamine ($R^3$=2-ethylhexyl) shall be derived by way of example without, however, limiting the invention.

Reacting the amine with the sulfinate and sulfonate in a molar ratio of 2:1:1, an equimolar mixture of 2-ethylhexylaminoethanesulfinate and 2-ethylhexylaminoethanesulfonate, $(2-C_2H_5-C_6H_{12})NHCH(CH_3)SO_2M$ and $(2-C_2H_5-C_6H_{12})NHCH(CH_3)SO_3M$, is obtained. A reaction of the amine with the sulfinate/sulfonate in a molar ratio of 1:1:1 gives an equimolar mixture of 2-ethylhexyliminoethane-sulfinate and -sulfonate, $(2-C_2H_5-C_6H_{12})N(CH(CH_3)SO_2M)_2$ and $(2-C_2H_5-C_6H_{12})N(CH(CH_3)SO_3M)_2$. Mixtures of aminoethane-sulfinate and -sulfonate with the starting sulfinate/sulfonate are obtained when the molar proportion of the amine is made smaller still. All these mixtures are likewise usable in the process of the invention.

Preference is given to using the sodium salts, particularly preferably the sulfinates $HOCH(CH_3)SO_2Na$, $H_2NCH_2SO_2Na$, $HN(CH_2SO_2Na)_2$, $N(CH_2SO_2Na)_3$, $H_2NCHCH_3SO_2Na$, $HN(CH(CH_3)SO_2Na)_2$, $N(CH(CH_3)SO_2Na)_3$, sodium 1-, 2-, 3-, 4-, 5-ethylhexylaminomethanesulfinate and also sodium 1-, 2-, 3-, 4-, 5-ethylhexylaminoethanesulfinate, the latter compounds being preparable by reaction of 1-, 2-, 3-, 4- or 5-ethylhexylamine with the sodium hydroxymethanesulfinate or sodium hydroxyethanesulfinate in equimolar ratios. If desired, these compounds can be used in mixture with the sulfonates, $HOCH(CH_3)SO_3Na$, $H_2NCH_2SO_3Na$, $HN(CH_2SO_3Na)_2$, $N(CH_2SO_3Na)_3$, $H_2N-CH(CH_3)SO_3Na$, $HN(CH(CH_3)SO_3Na)_2$, $N(CH(CH_3)SO_3Na)_3$, sodium 1-, 2-, 3-, 4-, 5-ethylhexylamino-methanesulfonate and -ethanesulfonate.

For the purposes of the invention, it is of course also possible, as exemplified above for the sulfonates in the schemes (a) and (b), to use "molecularly mixed" sulfinates/sulfonates. Scheme (c) exemplifies the nature of the compounds obtainable by specific reaction of ammonia with a hydroxyalkanesulfinate and the corresponding sulfonate—hereinafter referred to as $HOAlkSO_2$ and $HOAlkSO_3$:

(c) $NH_3+HOAlkSO_2 \rightarrow H_2NAlkSO_2+H_2O$   $H_2NAlkSO_2+ 2HOAlkSO_3 \rightarrow N(AlkSO_2)(AlkSO_3)_2+2H_2O$ or $NH_3+HOAlkSO_3 \rightarrow H_2NAlkSO_3+H_2O$   $H_2NAlkSO_3+ 2HOAlkSO_2 \rightarrow N(AlkSO_3)(AlkSO_2)_2+2H_2O$ It may additionally be noted that, of course, incomplete reaction or an excess of ammonia may mean that, as well as the products recited in scheme (c), residues of the starting or corresponding imino compounds are also be present. These considerations apply, mutatis mutandis, also to the use of primary amines instead of ammonia.

As well as the above-discussed components dithionite/acid acceptor or sulfinate opt. mixed with sulfonate, the aftertreatment compositions to be used in the process of the invention can include further additives. For instance, at least one hydroxyketone or an oligomer or polymer derived from a plurality of identical or different hydroxyketones can be added. The proportion of these compounds in the total mix is preferably 5–60% by weight.

These substances include, for example, acetoin $((H_3C)CH(OH)CO(CH_3))$, hydroxyacetone, cyclic compounds such as

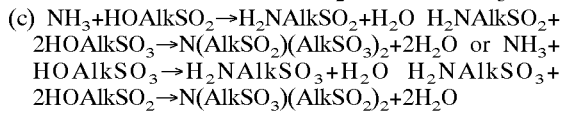

but also reductive acid,

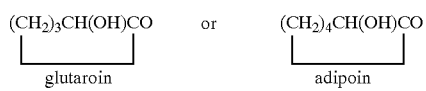

and ascorbic acid.

Further possible additives according to the invention include as monosaccharides aldoses such as erythrose, threose, ribose, xylose, arabinose, glucose, mannose, galactose or ketoses such fructose or sorbose.

Oligo- or polymeric hydroxyketones for the purposes of the invention are preferably the corresponding oligo- or polysaccharides. Specific examples are the disaccharides sucrose, lactose, maltose, cellobiose or trisaccharides such as raffinose and maltotriose. It is also possible to use starches which, chemically, are polysaccharides predominantly based on the monomeric glucose unit, and their partial hydrolysis products. For example, hydrolysis of the starch constituents amylose and amylopectin ultimately gives maltose and glucose. For the use of the aftertreatment compositions in the process of the invention, therefore, the admixture of hydrolyzable oligo- and polysaccharides is effective for producing an additional acid-binding effect. The aftertreatment composition preferably includes hydroxyacetone, acetoin, glutaroin or adipoin, particularly preferably glucose, fructose or sucrose, alone or else mixed.

The aftertreatment composition may further include at least one dispersant or surfactant or mixtures thereof. Their proportion in the total mixture is preferably 2–50% by weight. These auxiliaries can be cationic, anionic, nonionic or zwitterionic compounds. Suitable dispersants for the invention—without the sequence in the following list being construed as an allocation to one of these classes—are polycarboxylates and copolymers obtainable for example under the brand names of Sokalan® or Elvacite® or else "hyperdispersants" marketed under the name of Solsperse®, also condensates based on aromatic or alkylaromatic sulfonates obtainable under the brand names of Tamol® and Nekal® and also Supragil® and Rhodacar®.

Examples of surfactants to be used are:
alkoxylation products based on aliphatic or alkylaromatic hydroxy, amine and aminohydroxy compounds and commerically obtainable under the brand names of Synperonic® and Ukanil®, Dehypon®, Neopol®-Ethoxylate, Emulan®, Lutensol®, Plurafac® and Pluronic® or Elfapur®,
polyalkylene glycols, known under the brand names of Pluriol® and Antarox®,
aliphatic and alkylaromatic mono- and polysulfonates having the brand names Lutensit®, Rhodacar®, Rhodapon® and Teepol®,
esters and amides, for example sulfosuccinic esters of the brand Elfanol®,
partial phosphoric esters marketed under the names of Rhodafac® or else Marlophor®,
fatty acid partial glycerides and also fatty acid alkanolamides, to be obtained under the brand names of Luwitor® and Marlamid®, respectively,
and the surfactants available under the names of Plantaren® and Glucopon®.

It is further particularly advantageous to use surfactants having betaine or sultaine groups, ie. surfactants which are inner salts of quaternary ammonium and carboxylate (betaine) or sulfonate (sultaine) ions, obtainable for example under the brand name of Mackam®. It is also possible to use cationic surfactants based on quaternary ammonium compounds and amine oxides, available for example under the names of Alkaquat® and Rhodaquat® and also Mackalene®, Mackernium®, Mackpro® and Mackamine®.

The aftertreatment composition may further include as additive at least one ammonium, alkali metal or alkaline earth metal sulfite, bisulfite (hydrogensulfite) or disulfite. Their proportion in the overall mixture is 5–30% by weight. It is advantageous to use the alkali metal salts, especially $Na_2SO_3$, $NaHSO_3$ or $Na_2S_2O_5$.

If necessary, corrosion inhibitors can be included as well. The amounts thereof vary of course with the nature of the inhibitor within the range from 1 ppm to 1% by weight, based on the total mixture.

Preference is given to using an amount of from 5 ppm to 0.5% by weight, particularly preferably to a proportion of from 10 ppm to 0.1% by weight, again based on the total mixture. Suitable ingredients are substances from the following groups:
(a) reaction products of saturated or unsaturated aliphatic carboxylic acids having from 3 to 30 carbon atoms and aliphatic oligoamines having from 2 to 8 nitrogen atoms, which can additionally bear hydroxyl groups, or dialkanolamines or derivatives of such reaction products,
(b) aliphatic sulfonium salts, which can be substituted by additional hydrophilic groups,
(c) aliphatic or aromatic monocarboxylic acids and/or dicarboxylic acids having from 3 to 16 carbon atoms or their water-soluble salts,
(d) triazoles or derivatives thereof,
(e) imidazoles or derivatives thereof,
(f) thiazoles or derivatives thereof,
(g) unsaturated aliphaic alcohols having from 3 to 6 carbon atoms,
(h) alkenylsuccinic acid, its water-soluble salts or derivatives of such alkenylsuccinic acids,
(j) polymaleic acids or their water-soluble salts,
(k) α-olefin-maleic anhydride copolymers,
(l) sulfamidocarboxylic acids or their water-soluble salts and/or
(m) ammonium salts of sulfonic acids.

The substances of group (a) and their preparation are known for example from EP-A 034 726, DE-A 3 109 826, DE-A 3 109 827, EP-A 103 737 and German Patent Application 195 202 69.4.

Examples of compounds of group (b) and processes for their preparation are described in JP-B 1972/10202, DE-A 1 806 653 and DE-A 2 208 894.

Suitable inhibitors of group (c) include in particular aliphatic monocarboxylic acids having from 5 to 12 carbon atoms and/or their sodium and potassium salts and aliphatic dicarboxylic acids having from 4 to 12 carbon atoms and also their mono- or disodium or mono- or dipotassium salts. This group further includes aromatic carboxylic acids such as benzoic acid, methylbenzoic acid, phthalic acid and terephthalic acid and also their sodium and potassium or else ammonium salts, based for example on piperazine or morpholine.

Suitable triazoles (d) are especially hydrocarbyltriazoles, especially benzotriazole and toluotriazole.

Suitable imidazoles (e) are in particular unsubstituted imidazole, alkyl- or aryl-substituted imidazoles such as 1-($C_1$- to $C_4$-alkyl)imidazoles or 1-phenylimidazole, aminoalkylimidazoles, for example N-(3-aminopropyl) imidazole, and also quaternized imidazoles, for example N-vinylimidazole quaternized with dimethyl sulfate, the latter being described in German Patent Application 196 05 509 as nonferrous metal corrosion inhibitors.

Suitable thiazoles (f) are in particular hydrocarbylthiazoles, for example benzothiazole.

A typical representative of unsaturated alcohol (g) is propargyl alcohol.

The alkenylsuccinic acids (h) and their derivatives are in particular ammonium salts of alkenylsuccinic monoamides as described in DE-A 41 03 262. A particularly interesting alkenyl radical is polyisobutyl.

Suitable polymaleic acids (j) are described in EP-A 065 191, for example.

Typical α-olefin-maleic acid copolymers (k) are present partly or wholly opened to the dicarboxylic acid structures and are usually derivatized with amines to form amides or imides. Suitable α-olefins are in particular those having from 4 to 20 carbon atoms, for example isobutene, 1-octene or 1-dodecene.

Examples of sulfamidocarboxylic acids (l) are sulfonamides of anthranilic acid and also neutralization products of sulfamido-carboxylic acids with alkanolamines, dialkanolamines or trialkanolamines.

Suitable ammonium salts of sulfonic acids (m) include, for example, corresponding salts of 2-aminoethansulfonic acid (taurine).

Of course, the additives mentioned can be added not just alone but also in mixture, in which case the sum total of the proportions of the components in the aftertreatment composition has to add up to 100% by weight.

Furthermore, the aftertreatment composition can be used not only in dissolved but also in solid form, the solid form being preferred in the case of the dithionite-based aftertreatment composition.

It is customary to add from 0.1 g to 5.0 g of the aftertreatment composition, based on the solids content, per liter of the dyeing liquor or wash bath volume.

In the high temperature exhaust process, the textiles are dyed for example at 120–140° C. in pressure vessels, which are only safe to open when back at atmospheric pressure, at temperatures below 100° C. Otherwise, the reduction clearing of the polyester textiles proceeds at a satisfactory rate not only in the dyeing liquor but also in wash baths only at above about 50° C. The preferred temperature range for the aftertreatment is therefore 50–100° C.

The duration of the aftertreatment was 5–20 min in the recited illustrative embodiments, but different durations can also result under actual service conditions. These durations are influenced by parameters such as, for example, the temperature, the volume of the dyeing liquor or of the wash bath and, not unconnectedly, the efficiency of the mixing-in of the aftertreatment composition, but of course also by the nature of the colorant used.

The present invention further provides mixtures comprising at least one compound of the formula (Ia)

and a synergistically effective amount of at least one compound of the formula (II)

where

A is $NR^3{}_{3-q}$ or $OR^4{}_{2-p}$ $R^1$, $R^2$, $R^4$ are each hydrogen or $C_1$–$C_6$-alkyl $R^3$ represents identical or different radicals selected from the group consisting of hydrogen, $C_1$–$C_{20}$-alkyl, $C_3$–$C_8$-cycloalkyl opt. substituted by from one to three $C_1$–$C_4$-alkyl radicals M is the equivalent of an ammonium, alkali metal or alkaline earth metal ion p is 1 or 2 q is 1, 2 or 3 subject to the proviso that at least one of $R^1$, $R^2$ and $R^4$ is $C_1$–$C_6$-alkyl when A is $OR^4{}_{2-p}$.

Examples of corresponding mixtures and sulfonates were mentioned above in the description of the process of the invention.

Here too it is of course again possible to use "molecularly mixed" sulfinates/sulfonates.

The sulfinates and sulfonates are preferably used in a molar ratio within the range from 20:1 to 1:20, which means, mutatis mutandis, in relation to the "molecularly mixed" compounds that the molar ratio of sulfinate to sulfonate groups is preferably within the range from 20:1 to 1:20. In both cases the ratio is especially within the range from 10:1 to 1:10.

Preference is further given to mixtures wherein component (Ia) is at least one compound selected from the group consisting of $HOCH(CH_3)SO_2Na$, $H_2NCH_2SO_2Na$, $HN(CH_2SO_2Na)_2$, $N(CH_2SO_2Na)_3$, $H_2NCH(CH_3)SO_2Na$, $HN(CH(CH_3)SO_2Na)_2$, $N(CH(CH_3)SO_2Na)_3$ and sodium salts of 1-, 2-, 3-, 4- and 5-ethylhexylamino-methansulfinic acid and -ethanesulfinic acid and component (II) is selected from the group $HOCH(CH_3)SO_3Na$, $H_2NCH_2SO_3Na$, $HN(CH_2SO_3Na)_2$, $N(CH_2SO_3Na)_3$, $H_2NCH(CH_3)SO_3Na$, $HN(CH(CH_3)SO_3Na)$, $N(CH(CH_3)SO_3Na)_3$ and sodium salts of 1-, 2-, 3-, 4- and 5-ethylhexylamino-methanesulfonic acid and -ethanesulfonic acid.

These mixtures can include as further additives at least one hydroxyketone or an oligomer or polymer derived from a plurality of identical or different hydroxyketones, for example in a proportion of 5–60% by weight of the total mixture, at least one dispersant or surfactant or a mixture thereof, for example in a proportion of 2–50% by weight of the total mixture, and at least one ammonium, alkali metal or alkaline earth metal sulfite, bisulfite or disulfite, for example in a proportion of 5–30% by weight of the total mixture.

The additives mentioned can of course be added alone or in mixture, in which case the weight proportions of the components in the aftertreatment composition again have to add up to 100%. Examples of additives to be used in each case and of substances whose use is preferred were described above and are likewise used in the claimed mixtures.

If necessary, the mixtures may include further components such as the abovementioned corrosion inhibitors, for example in amounts from $10^{-4}$ to 1% by weight based on the total mixture of the aftertreatment composition.

The sulfinate mixtures of the invention are preferably used in the form of aqueous solutions for reduction clearing dyed or printed polyester textiles.

In addition, such mixtures, or else their aqueous solutions, can be used generally for cleaning polyester textiles. In this case, the noncolorant impurities would be decolorized by reduction.

Applications in resist printing are also possible, in which case the areas of the substrate which are not to be colored are treated with such mixtures or their solutions.

The dithionite-based aftertreatment composition is preferably used in solid form in the process of the invention. However, the use of aqueous solutions is also possible here.

When dispersants and/or surfactants are used in the liquid or dissolved state, this need not conflict with a solid formulation of the aftertreatment composition. Provided the remaining components are present in solid form, which will generally be the case with dithionites, acid acceptors, hydroxyketones and corrosion inhibitors, the binding capacity thereof will usually be sufficient to absorb a liquid or dissolved constituent, especially in the proportion of from 2 to 20% by weight of the total mixture claimed herein, to provide a granulable and/or free flowing product in most cases.

EXAMPLES

A. Dyeing

The dyeings were carried out by heating texturized polyester fabric with 4% by weight of the dye together with 1 g of a commercially available naphthalenesulfonic acid-formaldehyde condensate (Tamol®NOP) as dispersant and 0.5 g of nitrilo-triacetic acid salt (Trilon®A92) as complexing agent—both amounts expressed on the basis of one liter of aqueous dyebath—in an acetic acid liquor having a pH of 4.5–5.0 from initially 70° C. to 130° C. at a heat-up rate of 1° C./min and leaving it at the final temperature for 60 min. The liquor ratio, the ratio of dye-bath volume in liters to polyester fabric (dry) in kilograms was 20:1.

Aftertreatment

On completion of the dyeing step, the aftertreatment composition was added to the cooling dyeing liquor at the temperature T and allowed to act on it for the time t. The different temperatures T in ° C. and treatment times t in minutes are listed in Table 1. For the various aftertreatment compositions, Table 1 indicates concentrations which are to be understood as the amount of the aftertreatment composition in grams relative to the volume of the dyeing liquor in liters (corresponds to the volume of the dyebath including polyester fabric). Finally, the dyebath was dropped and the dyed fabric was rinsed with cold water for 5 min.

Wash Test

The dyed polyester fabric, either only rinsed or additionally aftertreated after the dyeing step, was heated together with a piece of white polyamide fabric of the same dry weight in a waterbath at pH 5 and 70° C. for 30 min. The liquor ratio of bath to fabric was again 20:1. The effectiveness of the aftertreatment was graded visually according to the degree of staining of the originally white polyamide fabric. If it remained white, no bleeding of the dyed polyester fabric had taken place (rating ––). Correspondingly, minor or pronounced staining of the polyamide fabric was observed when the polyester fabric bled to a minor or pronounced extent, respectively (ratings + and – respectively).

TABLE 1

| | | | | Conc. | | | | | | | Dispersant | | | |
| | | T | t | ATC | | % by | Acid | % by | Hydroxy- | % by | or | % by | Final | |
| Ex. | Dye | (° C.) | (min) | (g/l) | Reductant | weight | acceptor | weight | ketone | weight | surfactant | weight | pH | Result** |
|---|---|---|---|---|---|---|---|---|---|---|---|---|---|---|
| 1 | RED | 80 | 10 | 1.0 | Hydrosulfite | 50 | $Na_2CO_3$ | 30 | Sucrose | 20 | — | — | 8.0 | + |
| 1a* | RED | 80 | 10 | 1.0 | Hydrosulfite | 100 | — | — | — | — | — | — | 3.0 | – |
| 2 | BLUE | 70 | 20 | 2.0 | Hydrosulfite | 50 | $Na_2CO_3$ | 10 | Glucose | 40 | — | — | 5.5 | + |
| 2a* | BLUE | — | — | — | — | — | — | — | — | — | — | — | 3.0 | – |
| 2b* | BLUE | 70 | 20 | 2.0 | Hydrosulfite | 100 | — | — | — | — | — | — | — | – |
| 3 | BLUE | 80 | 20 | 3.0 | Hydrosulfite | 35 | $Na_2CO_3$ | 20 | Glucose | 25 | Tamol NOP/ oxo alcohol | 10/10 | 7.0 | ++ |
| 4 | RED | 90 | 10 | 1.5 | Hydrosulfite | 40 | $K_2CO_3$ | 20 | Sucrose | 30 | Tamol NOP | 10 | 7.0 | ++ |
| 5a* | RED | 80 | 15 | 1.0 | $HOCH_2SO_2Na$ | 100 | — | — | — | — | — | — | 5.0 | + |
| 5b* | RED | 80 | 15 | 1.0 | $HOCH_2SO_2Na$/ $HOCH_2SO_3Na$ | 50/50 | — | — | — | — | — | — | 5.0 | + |
| 6a* | BLUE | 80 | 15 | 1.0 | $HOCH_2SO_2Na$ | 100 | — | — | — | — | — | — | 5.0 | + |
| 6b* | BLUE | 80 | 15 | 1.0 | $HOCH_2SO_2Na$/ $HOCH_2SO_3Na$ | 50/50 | — | — | — | — | — | — | 5.0 | + |
| 7 | BLUE | 80 | 15 | 2.0 | $N(CH_2SO_2Na)_3$/ $N(CH_2SO_3Na)_3$ | 50/50 | — | — | — | — | — | — | 7.0 | + |
| 8 | RED | 70 | 15 | 2.0 | $HN(CH_2SO_2Na)_2$/ $Na_2SO_3$ | 80/20 | — | — | — | — | — | — | 6.0 | ++ |
| 9a | BLUE | 90 | 10 | 1.0 | $N(CH_2SO_2Na)_3$ | 50 | — | — | Glucose | 30 | Tamol NOP | 20 | 5.0 | ++ |
| 9b | BLUE | 90 | 10 | 2.0 | $N(CH_2SO_2Na)_3$ | 50 | — | — | Glucose | 30 | Tamol NOP | 20 | 5.0 | ++ |
| 10a | RED | 70 | 15 | 1.5 | Na-2-ethylhexyl-aminomethane-sulfinate | 100 | — | — | — | — | — | — | 6.0 | ++ |
| 10b | RED | 70 | 20 | 2.0 | Na-2-ethylhexyl-aminomethane-sulfinate | 100 | — | — | — | — | — | — | 6.0 | ++ |
| 11 | BLUE | 70 | 20 | 2.0 | Na-2-ethylhexyl-aminomethane-sulfinate | 100 | — | — | — | — | — | — | 6.0 | ++ |
| 12 | RED | 80 | 15 | 0.66[1] | $N(CH_2SO_2Na)_3$/ $HOCH(CH_3)SO_3Na$ | 90/10 | — | — | — | — | — | — | 6.0 | ++ |
| 13 | BLUE | 80 | 15 | 0.66[1] | $N(CH_2SO_2Na)_3$/ $HOCH(CH_3)SO_3Na$ | 90/10 | — | — | — | — | — | — | 6.0 | ++ |
| 14 | RED | 80 | 15 | 0.88[2] | $N(CH_2SO_2Na)_3$/ $N(CH_2SO_3Na)_3$/ $HOCH(CH_3)SO_3Na$ | 40/50/10 | — | — | — | — | — | — | 6.0 | ++ |
| 15 | BLUE | 80 | 15 | 0.88[2] | $N(CH_2SO_2Na)_3$/ $N(CH_2SO_3Na)_3$/ $HOCH(CH_3)SO_3Na$ | 40/50/10 | — | — | — | — | — | — | 6.0 | ++ |
| 16 | RED | 80 | 15 | 0.88[2] | $N(CH_2SO_2Na)(CH_2SO_3Na)_2$ | 100 | — | — | — | — | — | — | 6.0 | ++ |
| 17 | RED | 80 | 15 | 0.44[2] | $N(CH_2SO_2Na)(CH_2SO_3Na)_2$ | 100 | — | — | — | — | — | — | 6.0 | ++ |

RED: C.I. Disperse Red 54:1
BLUE: C.I. Disperse Blue 56
*Comparative example; no aftertreatment in 2a
[1] 2 g/l of a 33% strength aqueous solution
[2] 2 g/l of a 44% strength aqueous solution
**++ no staining
+ minor staining
– pronounced staining The examples recited in Table 1 show that the process of the invention provides excellent fastness improvements on polyester textiles. In addition, the hitherto customary time and energy-intensive sequence of dyeing, washing after dyeing, alkaline reduction clearing and a further final after-wash can be reduced to the pure dyeing step, followed by the addition of the aftertreatment composition to the dyeing liquor and a subsequent washing step. A further advantage of the process of the invention is the distinct reduction in the salt loadings (predominantly $Na_2SO_4$) compared with the conventional process, even for dithionite-based aftertreatment compositions (Examples 1–4).

B. Aftertreatment of Printed Polyester Fabrics/Preparation of Printed Patterns

The substrate used was a 90 g/m² satin grade polyester fabric from Synteen. A template was used to produce printed patterns 20×20 cm in size with a degree of coverage of 80%. 20% of the substrate remained unprinted in the form of four spots (white ground).

The two print pastes used contained per 1 kg of water:
10 g of sodium m-nitrobenzenesulfonate,
2 g of citric acid,
7 g of oleoylbisethanolamide,
30 g of the dispere dye Disperse Red 91 (paste "RED") or
30 g of the disperse dye Disperse Blue 148 (paste "BLUE")
and also bean flour ether as thickener to set a finished-paste viscosity of 40 dPas (determined by Haake VT 02 viscometer).

To produce the prints, the pastes were applied to the substrates using a commercially available screen printing machine and fixed with superheated steam at 180° C. for 8 minutes.

Reductive Wash

To remove the thickener, the printed fabrics were rinsed for 5 minutes with water rendered alkaline with 1.5 g of NaOH per liter. Immediately thereafter the reductive wash took place in a WBRG7 washer from AHIBA AG, at 70° C. for a duration of 5 minutes. Each of the printed polyester fabrics was used together with 400 ml of an aqueous solution of the aftertreatment composition recited in Table 2 as wash bath liquid. Following the reductive wash, the hue of the treated print, or its hue change, and also the staining of the white ground were inspected. The color of the wash bath was assessed as a further criterion. If the wash bath is colorless, the excess disperse dye not dissolved in the fiber, but adhering on the polyester fiber, was completely destroyed and therefore cannot color (stain) the white ground.

Table 2 compares the wash according to the invention with the customary polyester wash or the wash rendered obvious by the prior art.

TABLE 2

| Ex. | Dye | T. (° C.) | t (min) | Conc. ATC (g/l) | Reductant | Aftertreatment composition (NBM) | | | pH | Result** |
| | | | | | | % by weight | Acid acceptor | % by weight | | |
|---|---|---|---|---|---|---|---|---|---|---|
| 1a | RED | 70 | 5 | 1.94 | $N(CH_2SO_2Na)_3$/ $HOCH(CH_3)SO_3Na$# | 92.8/7.2 | — | — | 6.0## | ++ |
| 1b | BLUE | 70 | 5 | 1.94 | $N(CH_2SO_2Na)_3$/ $HOCH(CH_3)SO_3Na$# | 92.8/7.2 | — | — | 6.0## | ++ |
| 1a* | RED | 70 | 5 | 4.0 | Hydrosulfite | 50 | NaOH | 50 | 13.0 | + |
| 1b* | BLUE | 70 | 5 | 4.0 | Hydrosulfite | 50 | NaOH | 50 | 13.0 | + |
| 2a* | RED | 70 | 5 | | $HOCH_2SO_2Na$ | | — | — | 6.0 | + |
| 2b* | BLUE | 70 | 5 | | $HOCH_2SO_2Na$ | | — | — | 6.0 | + |
| 3a* | ROT | 70 | 5 | | $HOCH_2SO_2Na$/ $HOCH_2SO_3Na$ | | — | — | 6.0 | + |
| 3b* | BLUE | 70 | 5 | | $HOCH_2SO_2Na$/ $HOCH_2SO_3Na$ | | — | — | 6.0 | + |

RED: Disperse Red 91
BLUE: Disperse Blue 148
*Comparative example
**++ no hue change, wash bath colorless for long period, no dyeing of the white ground
+ hardly any hue change, rapid coloring of wash bath
used as 70% strength aqueous solution
pH set with 2 g of citric acid and aqueous sodium hydroxide solution

We claim:

1. A process for reduction clearing dyed or printed polyester textiles, which comprises adding, to the acidic dyeing liquor or the wash bath, an aftertreatment composition comprising as components a) at least one compound of the formula (I)

$$A_m[(CR^1R^2)_mSO_2M]_{p,q} \quad (I)$$

where
A is $NR^3_{3-q}$ or $OR^4_{2-p}$
p,q means q when A is $NR^3_{3-q}$, and p when A is $OR^4_{2-p}$
$R^1$, $R^2$, $R^4$ are each hydrogen or $C_1$–$C_6$-alkyl
$R^3$ represents identical or different radicals selected from the group consisting of hydrogen, $C_1$–$C_{20}$-alkyl, $C_3$–$C_8$-cycloalkyl opt. substituted by from one to three $C_1$–$C_4$-alkyl radicals
M is the equivalent of an ammonium, alkali metal or alkaline earth metal ion
m is 0 or 1
p is 1 or 2
q is 1, 2 or 3
subject to the provisos that at least one of $R^1$, $R^2$, $R^4$ is $C_1$–$C_6$-alkyl when A is $OR^4_{2-p}$ and that, if m is 0:
the compound of formula (I) is $S_2O_4M_2$, and
the compound of the formula (I) is used together with sufficient acid acceptor to raise the pH of the dyeing liquor or of the wash bath by from 1 to 3 units, c) optionally at least one compound of the formula (II)

$$A[CR^1R^2)SO_3M]_{p,q} \quad (II)$$

where A, $R^1$, $R^2$, $R^3$, $R^4$, M, p,q p and q are each as defined for the formula (I), although the specific choice of these variables does not have to be the same for the compounds of the formulae (I) and (II)

c) and optionally further additives.

2. A process as claimed in claim 1, wherein m is 0 and the compound of the formula (I) is added together with acid acceptors selected from the group consisting of bicarbonates, carbonates, oxides, hydroxides, bisulfites, sulfites, hydrogenphosphates and phosphates, of ammonium, alkali metals and alkaline earth metals.

3. A process as claimed in claim 1, wherein m is 0 and the compound of the formula (I) and the acid acceptor are used in a weight ratio within the range from 3:1 to 1:1.

4. A process as claimed in claim 1, wherein at least one compound of the formula (I) is used with at least one compound of the formula (II) in a molar mixing ratio within the range from 20:1 to 1:20.

5. A process as claimed in claim 1, wherein the aftertreatment composition includes as further additives at least
 ca) a hydroxyketone or an oligomer or polymer derived from a plurality of identical or different hydroxyketones, and/or
 cb) a dispersant or surfactant or a mixture thereof and/or
 cc) an ammonium, alkali metal or alkaline earth metal sulfite, bisulfite or disulfite.

6. A process as claimed in claim 5, wherein the additives are present in the total mixture of the aftertreatment composition in a proportion of
 ca) 5–60% by weight,
 cb) 2–50% by weight,
 cc) 5–30% by weight.

7. A process as claimed in claim 1, wherein the aftertreatment composition comprises as components
 a) at least one dithionite $S_2O_4M_2$ in a mixture with an acid acceptor selected from the group of the alkali metal and alkaline earth metal carbonates and bicarbonates,
 b) optionally at least one compound (II) selected from the group consisting of $HOCH(CH_3)SO_3Na$, $H_2NCH_2SO_3Na$, $HN(CH_2SO_3Na)_2$, $N(CH_2SO_3Na)_3$, $H_2NCH(CH_3)SO_3Na$, $HN(CH(CH_3)SO_3Na)_2$, $N(CH(CH_3)SO_3Na)_3$ and sodium salts of 1-, 2-, 3-, 4- and 5-ethylhexylamino-methanesulfonic acid and -ethanesulfonic acid, and
 c) optionally at least one further additive from the group of the mono- or disaccharides and/or a surfactant and/or a dispersant.

8. A process as claimed in claim 1, wherein the aftertreatment composition comprises as components
 a) at least one compound (I) selected from the group consisting of $HOCH(CH_3)SO_2Na$, $H_2NCH_2SO_2Na$, $HN(CH_2SO_2Na)_2$, $N(CH_2SO_2Na)_3$, $H_2NCH(CH_3)SO_2Na$, $HN(CH(CH_3)SO_2Na)_2$, $N(CH(CH_3)SO_2Na)_3$ and sodium salts of 1-, 2-, 3-, 4- and 5-ethylhexylamino-methanesulfinic acid and -ethanesulfinic acid, and
 b) optionally at least one compound (II) selected from the group consisting of $HOCH(CH_3)SO_3Na$, $H_2NCH_2SO_3Na$, $HN(CH_2SO_3Na)_2$, $N(CH_2SO_3Na)_3$, $H_2NCH(CH_3)SO_3Na$, $HN(CH(CH_3)SO_3Na)_2$, $N(CH(CH_3)SO_3Na)_3$ and sodium salts of 1-, 2-, 3-, 4- and 5-ethylhexylamino-methanesulfonic acid and -ethanesulfonic acid, and
 c) optionally at least one further additive from the group of the mono- or disaccharides and/or a surfactant and/or a dispersant.

9. A process as claimed in claim 1, wherein the aftertreatment composition is used in solid form.

10. A process as claimed in claim 1, wherein the aftertreatment composition is used in an amount based on the solids content within the range from 0.1 to 5.0 g per liter of the dyeing liquor or wash bath volume.

11. A mixture comprising at least one compound of the formula (Ia)

$$A[(CR^1R^2)SO_2M]_{p,q} \qquad (Ia)$$

and a synergistically effective amount of at least one compound of the formula (II)

$$A[CR^1R^2)SO_3M]_{p,q} \qquad (II)$$

where
 A is $NR^3_{3-q}$ or $OR^4_{2-p}$
 p,q means q when A is $NR^3_{3-q}$, and p when A is $OR^4_{2-p}$
 $R^1$, $R^2$, $R^4$ are each hydrogen or $C_1$–$C_6$-alkyl
 $R^3$ represents identical or different radicals selected from the group consisting of hydrogen, $C_1$–$C_{20}$-alkyl, $C_3$–$C_8$-cycloalkyl opt. substituted by from one to three $C_1$–$C_4$-alkyl radicals
 M is the equivalent of an ammonium, alkali metal or alkaline earth metal ion
 p is 1 or 2
 q is 1, 2 or 3,
although the specific choice of these variables does not have to be the same for the compounds of formulae (Ia) and (II); and optionally further additives.

12. A composition as claimed in claim 11, wherein components (Ia) and (II) are present in a molar ratio within the range from 20:1 to 1:20.

13. A mixture as claimed in claim 11, wherein component (Ia) is selected from the group consisting of $HOCH(CH_3)SO_2Na$, $H_2NCH_2SO_2Na$, $HN(CH_2SO_2Na)_2$, $N(CH_2SO_2Na)_3$, $H_2NCH(CH_3)SO_2Na$, $HN(CH(CH_3)SO_2Na)_2$, $N(CH(CH_3)SO_2Na)_3$ and sodium salts of 1-, 2-, 3-, 4- and 5-ethylhexylamino-methanesulfinic acid and -ethanesulfinic acid and
 component (II) is selected from the group $HOCH(CH_3)SO_3Na$, $H_2NCH_2SO_3Na$, $HN(CH_2SO_3Na)_2$, $N(CH_2SO_3Na)_3$, $H_2NCH(CH_3)SO_3Na$, $HN(CH(CH_3)SO_3Na)_2$, $N(CH(CH_3)SO_3Na)_3$ and sodium salts of 1-, 2-, 3-, 4- and 5-ethylhexylamino-methanesulfonic acid and -ethanesulfonic acid.

14. A mixture as claimed in claim 11, comprising as further additives
 ca) a hydroxyketone or an oligomer or polymer derived from a plurality of identical or different hydroxyketones, and/or
 cb) dispersant or surfactant or a mixture thereof, and/or
 cc) an ammonium, alkali metal or alkaline earth metal sulfite, bisulfite or disulfite.

15. A mixture as claimed in claim 14, wherein the additives are present in the total mixture of the aftertreatment composition in a proportion of
 ca) 5–60% by weight,
 cb) 2–50% by weight,
 cc) 5–30% by weight.

16. A process for the aftertreatment of reduction clearing dyed or printed polyester textiles comprising treating said textiles with an aqueous solution of the mixture as claimed in claim 11.

* * * * *

UNITED STATES PATENT AND TRADEMARK OFFICE
CERTIFICATE OF CORRECTION

PATENT NO. : 6,730,132 B1
DATED : May 4, 2004
INVENTOR(S) : Beckmann et al.

It is certified that error appears in the above-identified patent and that said Letters Patent is hereby corrected as shown below:

Title page,
Items [86] and [87], should read as follows:
-- [22]  PCT filed:       Jul. 14, 1997
   [86]  PCT No.:         PCT/EP97/03753
         § 371(c) (1),
         (2), (4) Date:   Jan. 22, 1999
   [87]  PCT Pub. No.:    WO 98/03725
         PCT Pub. Date:   Jan. 29, 1998 --

Column 1,
Line 3, should read as follows:
-- This Application is a 371 of PCT/EP97/03753, filed July 14, 1997. --

Signed and Sealed this

Twentieth Day of July, 2004

JON W. DUDAS
*Acting Director of the United States Patent and Trademark Office*